(12) United States Patent
Hörlin

(10) Patent No.: US 6,230,707 B1
(45) Date of Patent: May 15, 2001

(54) POWDER INHALER

(76) Inventor: Ernst Hörlin, Svartmossevägen 2, S-436 39 Askim (SE)

( * ) Notice: Subject to any disclaimer, the term of this patent is extended or adjusted under 35 U.S.C. 154(b) by 0 days.

(21) Appl. No.: 08/578,546

(22) PCT Filed: Jul. 25, 1994

(86) PCT No.: PCT/SE94/00704

§ 371 Date: Apr. 4, 1996

§ 102(e) Date: Apr. 4, 1996

(87) PCT Pub. No.: WO95/03846

PCT Pub. Date: Feb. 9, 1995

(30) Foreign Application Priority Data

Jul. 30, 1993 (SE) .................................................. 9302550

(51) Int. Cl.[7] .......................... A61M 15/00; A61M 16/00; B05D 7/14; B65D 83/06
(52) U.S. Cl. ................................ 128/203.15; 128/203.12
(58) Field of Search ......................... 128/203.15, 203.12, 128/203.23, 200.14, 200.11, 200.24, 204.25; 261/79.1, 79.2, DIG. 48

(56) References Cited

U.S. PATENT DOCUMENTS

| | | | | |
|---|---|---|---|---|
| 2,470,296 | * | 5/1949 | Fields | 128/203.15 |
| 2,470,297 | * | 5/1949 | Fields | 128/203.15 |
| 2,534,636 | * | 12/1950 | Stirn | 128/203.15 |
| 4,069,819 | * | 1/1978 | Valentini et al. | 128/203.15 |
| 4,841,964 | | 6/1989 | Hurka et al. | 128/203.15 |
| 5,301,666 | * | 4/1994 | Lerk et al. | 128/203.15 |
| 6,065,471 | * | 5/2000 | Schaffer et al. | 128/203.15 |

FOREIGN PATENT DOCUMENTS

| | | | |
|---|---|---|---|
| 215559 | * 7/1986 | (EP) | 128/203.12 |
| 20407028 | 1/1991 | (EP) . | |
| 10504459 | 9/1992 | (EP) . | |
| 12352556 | 12/1977 | (FR) . | |
| 461447 | 9/1971 | (JP) . | |
| 428426 | 7/1983 | (SE) . | |
| 19015635 | 12/1990 | (WO) . | |
| WO 94/19041 | * 9/1994 | (WO) | 128/203.12 |

* cited by examiner

Primary Examiner—John G. Weiss
Assistant Examiner—Joseph F. Weiss, Jr.

(57) ABSTRACT

The invention concerns an inhaler device (1) having a hollow tubular member (2, 102, 402) connected to a chamber (5, 105, 405). The tubular member has a first opening (3, 103, 203) at one end through which air can be sucked and the chamber (5, 105, 405) has a hole (4, 104, 204) therein for entry of air. When air is sucked through the first opening, air enters the chamber through the hole swirls and moves towards the first opening (3, 103, 203). To maintain or increase the swirling effect of the air a single restriction (10, 110) is arranged between the opening and the hole (4, 104, 204). A powdered substance (8) within the chamber is picked up by the swirling air within the chamber and is uniformly and finely divided by the swirling effect of the air. The effect can be enhanced by adding a movable element (6) such as a ball inside the chamber (5) and/or by providing a central core element (112, 412) inside the chamber.

10 Claims, 4 Drawing Sheets

IV-IV

V-V

POWDER INHALER

FIELD OF THE INVENTION

The present invention relates to an inhaler in accordance with the first part of claim 1. In particulart the invention relates to an inhaler for use with the inhalation of powdered medicinal substances.

BACKGROUND TO THE INVENTION

Various types of inhaler are known and widely used on the market. For example, many asthma sufferers regularly use a spray inhaler comprising a gas propellant which is stored in a metal container containing additionally a medicinal substance to be inhaled to ease the cause and or symptoms of the affliction. The metal container is connected in use to a hollow plastic carrier which at one end has a mouthpiece for the user. The device is operated by pressing the metal container inwardly with respect to said plastic carrier to thus release a pressurised dosage of medicine.

Such devices are however bad for the environment due to the use of propellants and other carrier gases. Additionally the amount of medicament which is inhaled comes from a store of medicine in the container suitable for many inhalations, such that considerable problems arise concerning the amount of each dose inhaled due to incomplete or uneven mixing of the medicament, or due to variations in the available gas pressure. Further dosage anomalies may also occur if the inhaler has been allowed to stand for a long period of time between uses. Moreover such inhalers are relatively bulky and expensive.

Also known are inhalers which have a body portion containing an impeller blade or fan incorporated therein and further including a compartment for the introduction of a medicament. On operation, said medicament is ejected by the action of the rising air flow caused by the fan.

Such inhalers have the disadvantage that an uneven flow often results and the construction of the device makes it relatively expensive, bulky and prone to breakage or malfunction.

A further known inhaler having the features defined in the preamble of claim 1 is disclosed in U.S. Pat. No. 4,069,819. The inhaler device of this document however presents difficulties in normal operation because powder is withdrawn slowly from the capsule within the capsule chamber, partly due to the small diameter of the holes which are possible in the capsule due to the design of the device and partly due to the limited movement of the capsule in the chamber. The capsule is restrained in the longitudinal direction by an intermediate wall containing a plurality of holes and comprising a semi-spherical lower surface which is on a wider arc than that of the capsule upper end to thereby allow rotational procession of the capsule thereagainst without substantial hindrance, whilst still allowing powder to reach the user.

The powder entering the mouthpiece is thus confined to a substantially laminar flow such that the dispersion/separation thereof is minimal and the sucking effort required will often be quite large. Moreover one or more of the plurality of passages will often be blocked by the capsule leading to particle build-up and clogging.

OBJECT OF THE INVENTION

The object of the present invention is therefore to overcome the problems of the prior art devices by providing an inhaler which is simple and reliable for use with powder substances and which further provides good dispersion characteristics so that the powder more easily reaches the lungs.

A further object of the invention is to provide a device which is suitable for use with an amount of medicament for only one use under full control of the user.

A still further object of the invention is to provide a device which is relatively inexpensive and thus readily disposable.

Further objects and advantages of the invention will become apparent to the skilled man upon studying the following description and drawings of a preferred embodiment.

SUMMARY OF THE INVENTION

The invention has the features defined in claim 1 appended hereto. Preferred features of the invention are defined in the dependent claims.

By the use of a single restriction in accordance with claim 1 the velocity upon exiting the chamber will increase and a swirling effect upon air passing from the chamber into the tubular member can be maintained which leads to better dispersion characteristics.

DESCRIPTION OF PREFERRED EMBODIMENTS

Figure 1:
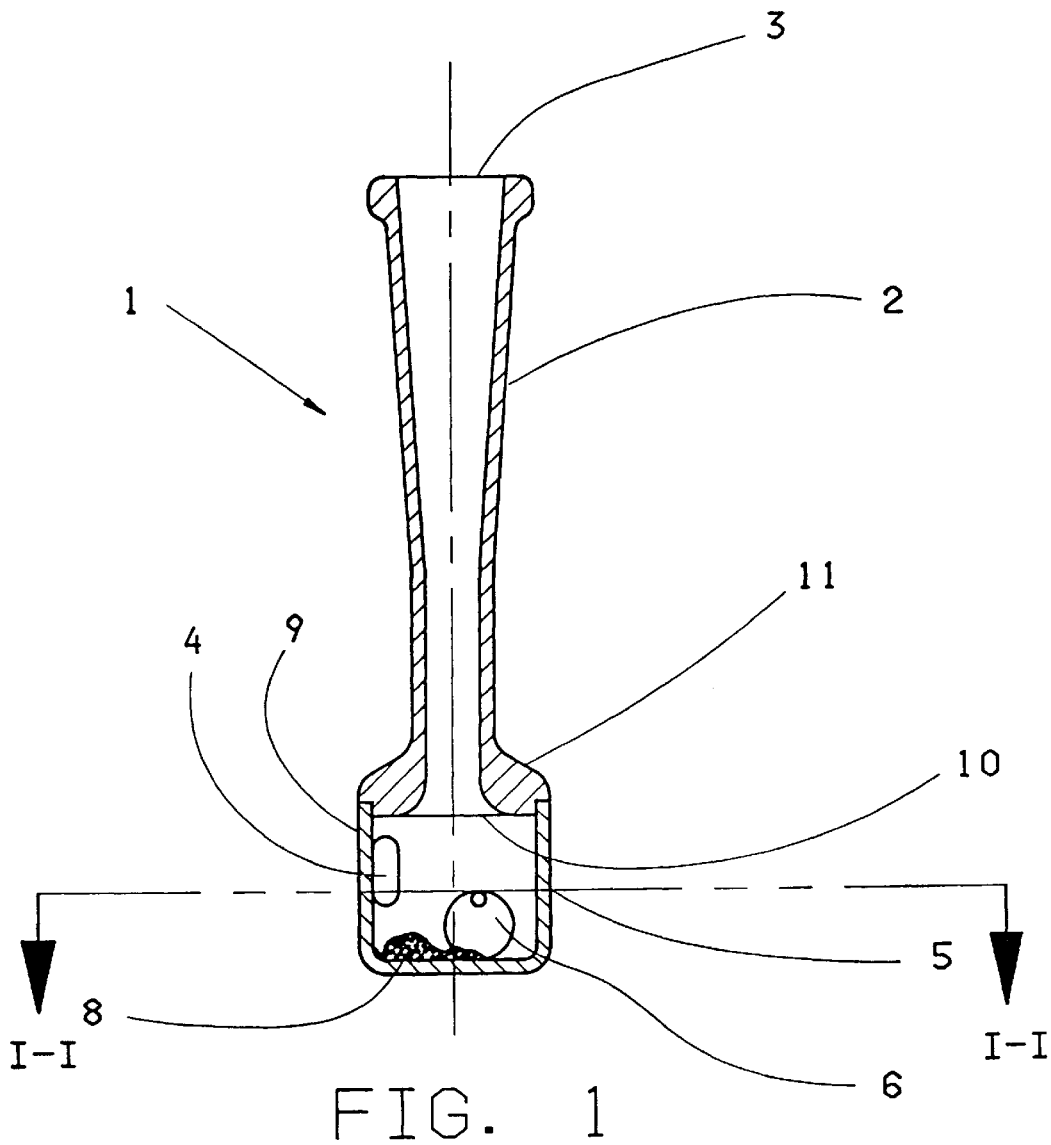
FIG. 1 shows a cross-section through one embodiment of a device according to the invention.

FIG. 1 shows a two-part inhaler device 1 which comprises a tubular member 2 which has a first opening 3 at one end and a second opening 10 at the other end connected to a chamber 5. In between the first opening 3 and the planar end wall of the chamber 5 the device 2 is hollow as shown in the figures.

An opening 4 is also provided in the chamber 5 and serves as a passageway to connect the inside of the chamber 5 with the surrounding air.

The tubular member 2 of the device 1 is formed as a mouthpiece designed to be held within the lips of a user, the mouthpiece preferably being inserted into the user's mouth so that the lips of the user will rest on the smooth curved surface 11.

A freely movable element 6, preferably in the form of a sphere, is positioned inside the chamber.

Whilst a two-piece device is shown, a one-piece device or a device having more pieces is also possible. Similarly the material may be chosen as required by the circumstances. For most applications it will be possible to construct the device from plastics material such as e.g. transparent plastics material or PVC. If desired the number of passageways 4 may be increased.

Figure 2:
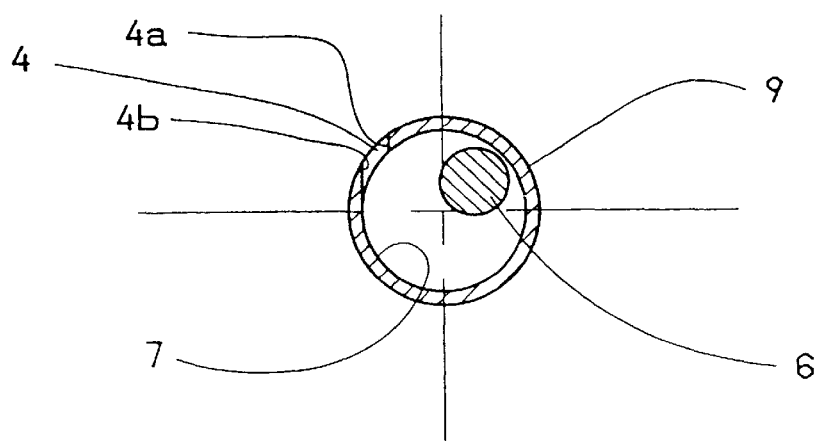
FIG. 2 shows a cross-section through the device taken along line II—II of FIG. 1.

The passageway 4, as best seen in FIG. 2 consists of an opening formed in the wall of the chamber 5. The opening 4 is formed appropriately so as to cause the air entering the chamber to swirl around the chamber. In the shown embodiment the sides 4a, 4b are offset from the central rotational axis of the chamber such that the outer side 4b is substantially tangential to the inner wall 7 of the chamber. The inner wall is substantially cylindrical and circular, although it may be foreseen with projections or another type of surface profile (e.g. a roughened surface).

Figure 7:
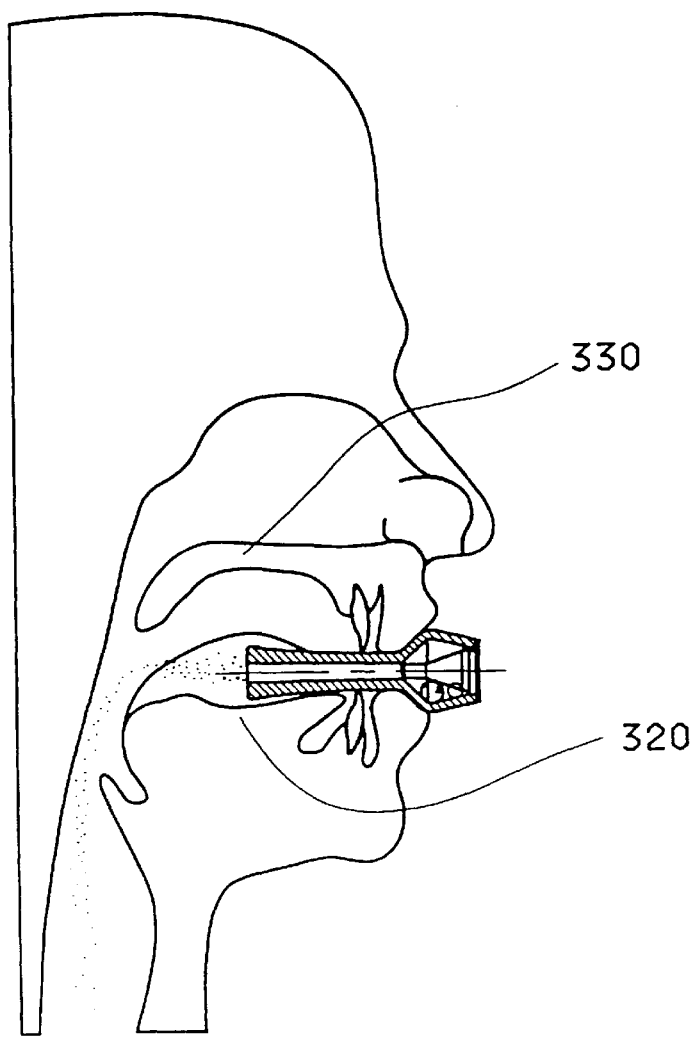
FIG. 7 shows a cross-sectional view of the device according to FIG. 3 in the position of use within the mouth of a user.

The chamber 5 of this embodiment, in use, will contain a quantity of substance 8 in dry powder form, normally a medicament, which is to be inhaled by the user who will put the mouthpiece to his lips and suck (see also FIG. 7).

Due to the sucking action, air will be drawn in through the opening 4 in the chamber (similar to an inverse whistle) and, due to the orientation of the opening 4, will circulate around the chamber 4 thus causing a swirling of the air therein. The element 6 will be caused to spin and to move under this swirling action of the air and will thus vibrate inside the chamber, in turn causing the powdered medicament to be taken along with the swirling air towards the opening 3 from where it exits into the user.

Figure 3:
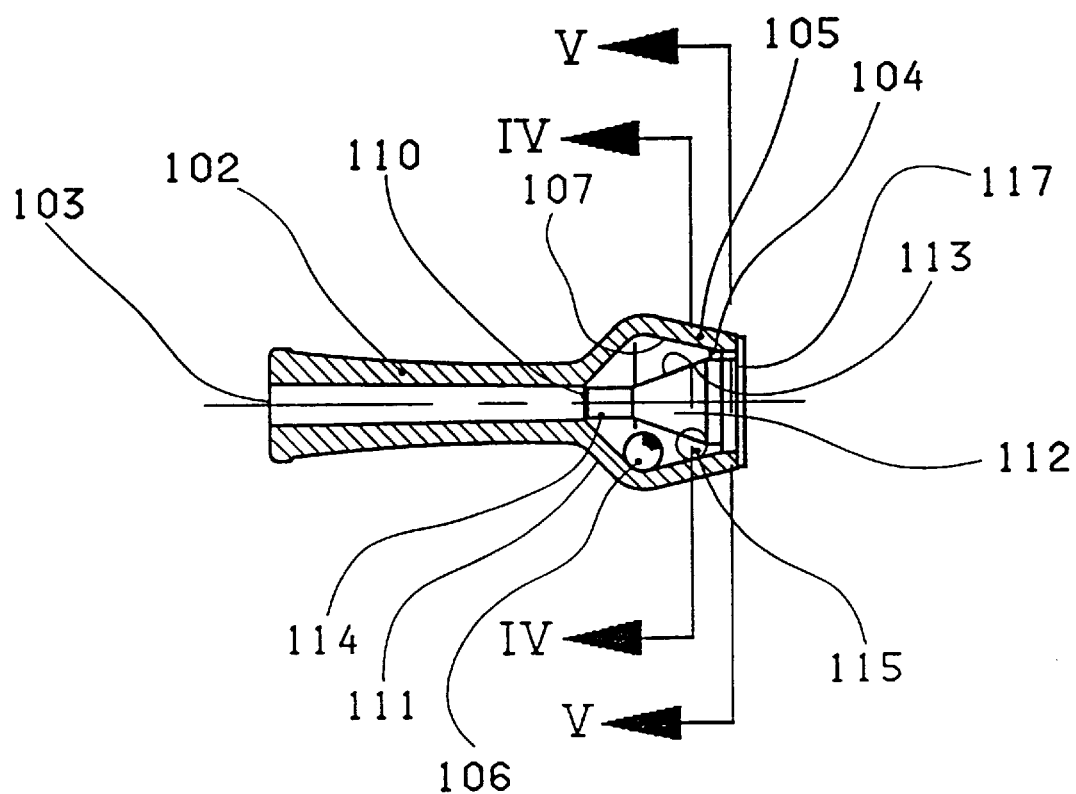
FIG. 3 shows a cross-section through a second embodiment of the invention.
Figure 4:
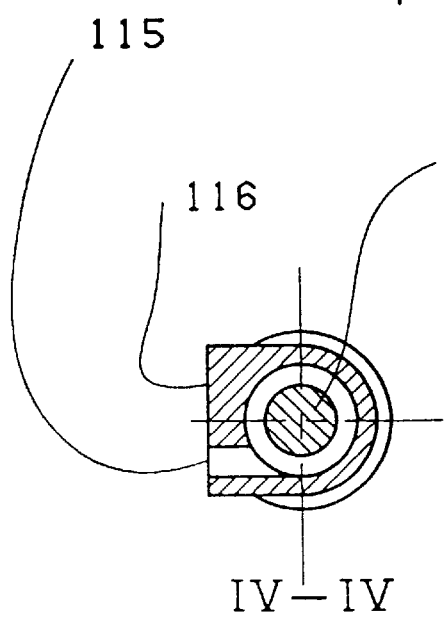
FIG. 4 shows a cross-section taken along line IV—IV in FIG. 3
Figure 5:
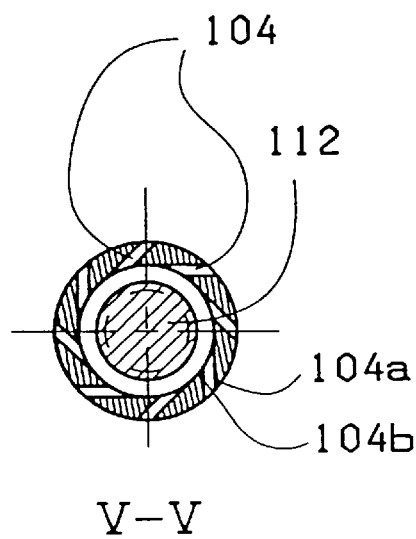
FIG. 5 shows a cross-section taken along line V—V in FIG. 3
Figure 6:
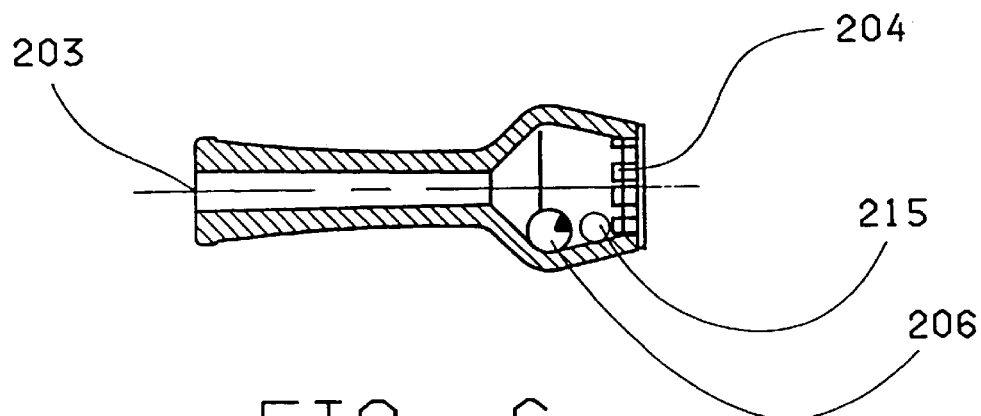
FIG. 6 shows a third embodiment of the invention.

Only a short suck, requiring small sucking effort, is required on the mouthpiece 3 to give the element 6 a high velocity around the chamber and thus to effect dispersal of the powder as required for inhalation. Due to the presence of only one restriction 10, in this case at the interface between the member 2 and the chamber 5, the turbulence and swirling of the air and powder will be maintained when passing from the chamber 5 to the tubular member 2. The restriction 10 will also cause the velocity of the air to increase as it exits the chamber which will increase inter-particle bombardment leading to a finer particle size of the powder substance 8. In this way any lumps of powder will be more uniformly dispersed.

If desired, the effect of the vibrations of the element 6 may be enhanced by providing roughening or other projecting members (e.g. ribs or serrations) on the inner surface 7.

In a further embodiment of the invention, the element 6 may itself contain the medicinal substance for inhalation, appropriate outlets being provided in the element. Alternatively the element 6 may consist of the substance to be inhaled, such that the substance, for example, breaks up into powder form upon vibration, although careful sizing of the restriction 10 is required.

With the device according to the invention, an efficient and environmentally-friendly inhaler is produced which is thus both simple and reliable.

Due to the relative cheapness of production of such a device, the device has suitability as a disposable device for once-only use, containing the quantity of medicament required for said one use. Typically such a quantity might be between 5 and 30 mg, typically 20 mg, although smaller or larger doses are possible. If the device is made in two parts as shown for example, the part 2 could be re-usable and part 9, corresponding to the chamber section 5, could be a disposable part. For reasons of hygiene, suitable removable or pierceable means to cover the opening 4 and the opening from the chamber into the part 2 at the restriction should be provided.

A further embodiment of the invention is shown in FIG. 3, like features being denoted with the same reference numerals as in the previous figure but increased by 100.

The inhaler device of this embodiment is made in one piece, the member 102 and the chamber 105 being combined and having a different shape. The shape of the chamber portion 105 is such that, starting from the end face 117 of the chamber and moving in a direction towards the member 102, the inner wall 107 of the chamber 105 has a section "a" defining an increasing cross-sectional area followed by a section "b" of decreasing cross-sectional area. This arrangement has the particular effect that air drawn in through the passageways 104 first undergoes a decrease in velocity due to the increasing cross-section in section "a" followed by a transition at the interface between sections "a" and "b" to an increasing velocity. By appropriate choice of angle of inclination of the sections "a" and "b", the air may also be caused to separate from the sidewall 107 to form eddy currents. The net effect of this is to cause a large amount of turbulence in the air in the chamber which will increase inter-particle bombardment and thus increase the uniformity of dispersion. The effect of this turbulence can be enhanced by the use of a further element 106, such as a ball (as explained with reference to FIG. 1).

The device is further fitted with a central core element 112 having preferably a trunconic portion 113 joined to a circular cylindrical portion 114 of constant diameter. The core element 112 may be formed as one piece with the end wall 117 or attached thereto as appropriate. The portion 114 extends up to the area of the restriction 110.

When air is sucked in through passageways 104, the turbulent effect caused by the sidewall shape is enhanced by the shape of the core element 112 which allows only a small area of the chamber to be "active" for air movement whilst still providing space for movement of the element 106 therein.

As can be seen from FIG. 3, the portion 114 extends up to the restriction 110 is such a way that a single, thin annular restriction is present around the outside of the core element 112. This further enhances the velocity increase at this point which gives a strong rotation of the air and powder substance at this location, in turn leading to further inter-particle bombardment (thus better uniformity of dispersion and lower particle size) and rotation along the member 2. Clogging at the restriction 110 is not a problem due to the high air velocity and at this point.

Thus in normal use, powder particles which are drawn into the swirling air will undergo the above described velocity changes of the air current due to their relatively low mass and will finely and uniformly disperse into the swirling air. Upon passing the restriction 110 the particles will then separate further along the gradually widening tubular element 2 and their velocity will decrease, which is important in order to allow the powder substance to be transported all the way to the user's lungs.

As also shown in FIG. 4, the inhaler device is provided with a further opening 115 which serves as an inlet for the powder substance to be inhaled. The powder substance would normally enter through the opening 115 from an external magazine (see FIG. 8), the powder being able to enter the chamber either before or during inhalation by the user.

As can be seen in FIG. 4, the powder is also arranged to enter tangentially into the chamber, the magazine device or the like being positioned against the flat abutment face 116 of the chamber wall.

FIG. 5 shows a cross-section of the lower end of the chamber 105 with eight passageways 104 arranged to allow air entry.

FIG. 6 depicts the same type of device as described with reference to FIG. 3, although with no central core element 112 but having a ball element 206 arranged for free rotation when air is sucked in through passageway 204 due to suction effort at 203. A magazine may be attached to allow powder entry through hole 215.

FIG. 7 depicts the preferred mode of use of the device, the lips of the user being placed against the lip abutment surface 111 and the opening 203 being positioned far enough back inside the mouth so that negligible powder is lost in the oral cavity (e.g. to the tongue 320 or palate 330) before entering the lungs. This has the further advantage that the taste sensors of the tongue are to a great extent unexposed to the medicinal substance which is relatively slow moving at this point.

Figure 8:
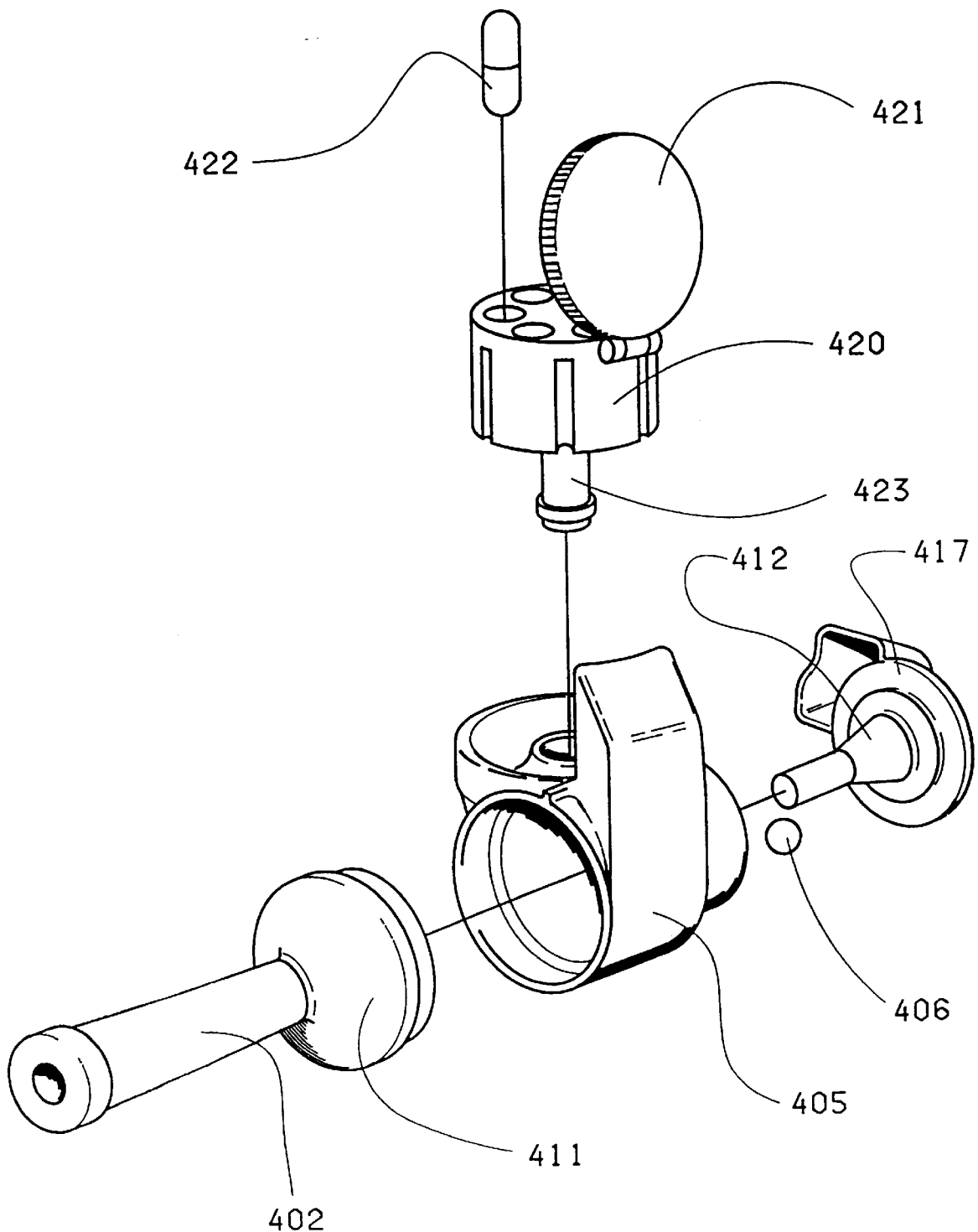
FIG. 8 shows an exploded view of a device according to the invention fitted with a capsule magazine.

In FIG. 8 an embodiment fitted with a capsule magazine is depicted as an exploded view. The elements correspond basically to the elements shown in FIG. 3, although the numerals are in a 400 series instead of 100 series. Thus no detailed explanation of operation is required since this will be the same as for previous embodiments.

The tubular member 402 and lip abutment surface 411 are formed as a one piece moulding which is attached to chamber 405 by a push fit or the like. A ball 406 is contained within the chamber 405 and the chamber is closed at its lower end by an end face 417 having integral core element 412. A magazine containing capsules 422, which in turn contain a quantity of powder substance (preferably equal to one dose), is attached by means of pipe 423 to the housing of chamber 405 and through which powder from a ruptured capsule can be transported. The actual details of the magazine are unimportant to the invention, any suitable type of magazine being possible. In the shown embodiment however the magazine is provided with a flip lid 421 attached by a hinge to the magazine body 420.

The relative sizes, weights and materials of the device are largely a matter of choice according to the circumstances and can be varied within large limits. One example of dimensions for the device may typically be where the length of the mouthpiece or tubular member from the opening 3 to the lip abutment surface 11 is between about 2 to 6 cm, with a chamber 5 diameter of between about 10 mm and 20 mm, preferably about 16 to 18 mm. With such dimensions, the width of the opening 4 between side faces 4a and 4b would typically be about 2 to 3 mm and the element 6 could be a sphere of about 3 mm radius. Clearly such dimensions provide a slim and compact unit.

When the device is made of clear plastics, the additional advantage obtained would be that the user can see whether all the medicament has been inhaled or not.

Whilst preferred embodiments of the invention have been described above it is clear that many variations of the invention are possible within the scope of the claims appended hereto.

What is claimed is:

1. An inhaler device comprising:

a hollow tubular member fluidically connected to a hollow chamber, wherein said tubular member is provided with a first opening at one end and wherein at least one entrance passageway is provided in said chamber, the at least one entrance passageway being arranged substantially tangentially with respect to said chamber so as to cause air sucked therethrough to swirl around said chamber, wherein a single restriction is arranged between the first opening and the at least one entrance passageway, wherein said chamber has an element therein which is sized so as to be randomly moveable in three dimensions within said chamber.

2. An inhaler device according to claim 1, wherein said chamber has a sidewall which is shaped so as to provide the chamber with a first portion an having increasing cross-sectional area in a direction towards said restriction and a second portion with a decreasing cross-sectional area in a direction towards said restriction.

3. An inhaler device according to claim 1 wherein said chamber has an inner wall which is substantially circular in cross-section.

4. An inhaler device according to claim 1, comprising a core element arranged within said chamber, said core element extending from an end wall of said chamber to a position proximate said single restriction.

5. An inhaler device according to claim 4, wherein said core element has a trunconic portion with its large end close to the end wall of said chamber and a constant-section cylindrical portion extending from the smaller end of said trunconic portion up to the area of the restriction.

6. An inhaler device according to claim 1, comprising a magazine for carrying a plurality of powder doses connected to the interior of said chamber by means of an inlet opening provided in the wall of said chamber.

7. An inhaler device according to claim 1, wherein said chamber contains a medicinal substance in powder form.

8. An inhaler device according to claim 1, wherein at least said chamber of said inhaler device comprises a transparent material.

9. An inhaler device according to claim 1, comprising a protruding portion on the exterior of the inhaler device at a distance of between about 2 cm and 6 cm from said first opening.

10. An inhaler device according to claim 1, wherein element contains a substance in powder form.

\* \* \* \* \*

UNITED STATES PATENT AND TRADEMARK OFFICE
CERTIFICATE OF CORRECTION

PATENT NO. : 6,230,707 B1  
DATED : March 15, 2001  
INVENTOR(S) : Ernst Horlin

It is certified that error appears in the above-identified patent and that said Letters Patent is hereby corrected as shown below:

Claim 2,
Line 3, delete "an".

Signed and Sealed this

Twenty-seventh Day of November, 2001

Attest:

*Nicholas P. Godici*

NICHOLAS P. GODICI  
*Attesting Officer*  *Acting Director of the United States Patent and Trademark Office*

UNITED STATES PATENT AND TRADEMARK OFFICE
CERTIFICATE OF CORRECTION

PATENT NO. : 6,230,707 B1
DATED : May 15, 2001
INVENTOR(S) : Ernst Horlin

It is certified that error appears in the above-identified patent and that said Letters Patent is hereby corrected as shown below:

<u>Claim 10,</u>
Line 2, "element" should be replaced with -- said element --.

Signed and Sealed this

Sixteenth Day of April, 2002

Attest:

JAMES E. ROGAN
*Director of the United States Patent and Trademark Office*

*Attesting Officer*